US010507321B2

(12) United States Patent
Young et al.

(10) Patent No.: US 10,507,321 B2
(45) Date of Patent: Dec. 17, 2019

(54) MULTILAYER STRUCTURE AND METHOD OF MANUFACTURING A MULTILAYER STRUCTURE (71) Applicant: MEDTRONIC BAKKEN RESEARCH CENTER B.V., Maastricht (NL)

(72) Inventors: Edward Willem Albert Young, Maastricht (NL); Gijs Peters, Eindhoven (NL); Erik van Veenendaal, Nuenen (NL)

(73) Assignee: Medtronic Bakken Research Center B.V., Mastricht (NL)

( * ) Notice: Subject to any disclaimer, the term of this patent is extended or adjusted under 35 U.S.C. 154(b) by 1057 days.

(21) Appl. No.: 14/952,585

(22) Filed: Nov. 25, 2015

(65) Prior Publication Data
US 2016/0144078 A1 May 26, 2016

Related U.S. Application Data (60) Provisional application No. 62/084,327, filed on Nov. 25, 2014.

(51) Int. Cl.
*A61N 1/05* (2006.01)
*A61L 31/02* (2006.01)
(Continued)

(52) U.S. Cl.
CPC ........ *A61N 1/0534* (2013.01); *A61B 5/04001* (2013.01); *A61L 31/026* (2013.01);
(Continued)

(58) Field of Classification Search
CPC .......... A61B 2562/12; A61B 2562/125; A61B 2562/22; A61B 2562/222;
(Continued)

(56) References Cited

U.S. PATENT DOCUMENTS 4,417,387 A 11/1983 Heslop
5,650,897 A 7/1997 Cohen et al.
(Continued)

FOREIGN PATENT DOCUMENTS

WO 9949934 A1 10/1999
WO 2006131912 A2 6/2007
WO 2010055453 A1 5/2010

OTHER PUBLICATIONS

Prosecution History U.S. Appl. No. 13/762,426, dated Jun. 30, 2014 through Oct. 7, 2016, 104 pp.
(Continued)

*Primary Examiner* — Lee S Cohen
*Assistant Examiner* — Erin M Cardinal
(74) *Attorney, Agent, or Firm* — Shumaker & Sieffert, P.A.

(57) ABSTRACT

In some examples, a medical device system a thin film including at least one electrically conductive track extending between at least one electrode and at least one electrical contact, a first and second polymer layer; wherein, at a portion of the thin film between the at least one electrode and the at least one electrical contact, the first polymer layer and second polymer layer surround the at least one electrically conductive track; and at least one discrete ceramic member located between the first and second polymer layers at a portion of the thin film between the at least one electrode and the at least one electrical contact, wherein the at least one discrete ceramic member does not surround the at least one conductive track, and wherein the at least one discrete ceramic member is configured to increase adhesion between the first polymer layer and second polymer layer.

22 Claims, 6 Drawing Sheets (51) Int. Cl.
*A61L 31/04* (2006.01)
*A61B 5/04* (2006.01)

(52) U.S. Cl.
CPC ....... *A61L 31/048* (2013.01); *A61B 2562/125* (2013.01); *A61L 2420/02* (2013.01); *A61L 2420/08* (2013.01)

(58) Field of Classification Search
CPC ............. A61B 2562/227; A61L 31/026; A61L 31/048; A61L 2420/02; A61L 2420/08; A61N 1/0534; A61N 1/04001
See application file for complete search history.

(56) References Cited

U.S. PATENT DOCUMENTS

| | | | |
|---|---|---|---|
| 5,683,442 | A | 11/1997 | Davidson |
| 6,208,881 | B1 | 3/2001 | Champeau |
| 6,844,023 | B2 | 1/2005 | Schulman et al. |
| 7,941,202 | B2 | 5/2011 | Hetke et al. |
| 8,484,841 | B1 | 7/2013 | Burros et al. |
| 8,805,542 | B2 | 8/2014 | Tai et al. |
| 2003/0022403 | A1 | 1/2003 | Shimoda et al. |
| 2003/0087197 | A1* | 5/2003 | Schulman ............ C23C 14/042 430/315 |
| 2005/0077630 | A1 | 4/2005 | Kirby |
| 2008/0058895 | A1 | 3/2008 | Ok et al. |
| 2008/0140152 | A1* | 6/2008 | Imran ................ A61N 1/0553 607/46 |
| 2008/0154365 | A1* | 6/2008 | Tai .................... B81C 1/0023 623/6.63 |
| 2008/0255439 | A1 | 10/2008 | Tang et al. |
| 2009/0177144 | A1* | 7/2009 | Masmanidis ...... A61B 5/04001 604/66 |
| 2010/0023102 | A1* | 1/2010 | Spruit ................ A61B 5/04001 607/116 |
| 2010/0331938 | A1 | 12/2010 | Sommer et al. |
| 2011/0093052 | A1 | 4/2011 | Anderson et al. |
| 2011/0224765 | A1 | 9/2011 | Harberts et al. |
| 2011/0230747 | A1* | 9/2011 | Rogers ..................... A61B 5/05 600/377 |
| 2011/0313269 | A1* | 12/2011 | Kim ................... A61B 5/04001 600/373 |
| 2013/0020431 | A1 | 1/2013 | Bennett et al. |
| 2013/0204318 | A1* | 8/2013 | Young .................. A61N 1/0534 607/45 |
| 2013/0345780 | A1* | 12/2013 | Tabada ..................... A61N 1/04 607/115 |
| 2015/0018659 | A1* | 1/2015 | Ware .................. A61B 5/04001 600/378 |
| 2015/0265835 | A1* | 9/2015 | Young .................. A61N 1/3754 600/544 |
| 2017/0080216 | A1* | 3/2017 | Pham .................. A61B 5/0478 |

OTHER PUBLICATIONS

Notice of Allowance from U.S. Appl. No. 13/762,426, dated Nov. 8, 2017, 8 pp.
Response to Office Action dated Oct. 7, 2016, from U.S. Appl. No. 13/762,426, filed Jan. 9 2017, 12 pp.
Office Action from U.S. Appl. No. 13/762,426, dated Apr. 26, 2017, 8 pp.
Response to Office Action dated Apr. 26, 2017, from U.S. Appl. No. 13/762,426, filed Jul. 26, 2017, 8 pp.

* cited by examiner

MULTILAYER STRUCTURE AND METHOD OF MANUFACTURING A MULTILAYER STRUCTURE

This application claims the benefit of U.S. Provisional Application Ser. No. 62/084,327, filed Nov. 25, 2014, which is incorporated herein by reference in its entirety.

TECHNICAL FIELD

The present disclosure relates, in some examples, to multilayer structures and methods of manufacturing a multilayer structure. Such multilayer structures may be used in medical devices, such as, e.g., implantable neurostimulation devices or other active implantable devices.

BACKGROUND

Implantable neurostimulation devices have been used to treat acute or chronic neurological conditions. Deep brain stimulation (DBS), the electrical stimulation of sub-cortical structures, belongs to this category of implantable devices, and has been shown, for example, to be therapeutically effective for Parkinson's disease, dystonia, and tremor. Applications of DBS in the domain of psychiatric disorders (e.g., obsessive compulsive disorder and depression) also exist.

SUMMARY

In some examples, the disclosure relates to an implantable stimulation lead for the delivery of electrical stimulation to a patient, e.g., to treat patient disorders. For example, the implantable electrical stimulation lead may be configured to be implanted in the brain of the patient to deliver DBS. A thin film may be used to form the lead with a an electrode at a distal portion and an electrical contact at a proximal portion, and at least one electrically conductive track extending between the electrode and electrical contact. The electrically conductive track(s) may electrically couple the electrical contacts at the proximal portion and the electrode at the distal portion. Between the electrode and electrical contact, a portion of the electrically conductive track(s) may be surrounded by a variety of materials including an outer polymer coating, e.g., to provide for biocompatibility of the lead for implantation within a patient. The outer polymer coating may include a first polymer layer and second polymer layer, different from the first polymer layer, which combine to surround the electrically conductive tracks between the electrode and electrical contact and are in direct contact with each other over a portion of the thin film. The thin film may further include at least one discrete ceramic member separate from the electrically conductive track(s) that is in direct contact with both the first and second polymer layers between the electrode and electrical contact to increase the adhesion between those polymer layers. In some examples, the lead may be configured to sense electrical activity of a patient in addition to, or as an alternative to, the delivery of electrical stimulation.

In one example, the disclosure relates to a medical device system configured to at least one of deliver electrical stimulation to a patient or sense electrical activity of the patient, the system comprising a thin film. The thin film includes at least one electrode, at least one electrical contact, at least one electrically conductive track extending between the at least one electrode and the at least one electrical contact, a first polymer layer; a second polymer layer, wherein, at a portion of the thin film between the at least one electrode and the at least one electrical contact, the first polymer layer and second polymer layer surround the at least one electrically conductive track; and at least one discrete ceramic member located between the first and second polymer layers at a portion of the thin film between the at least one electrode and the at least one electrical contact, wherein the at least one discrete ceramic member does not surround the at least one conductive track at the portion of the thin film between the at least one electrode and the at least one electrical contact, and wherein the at least one discrete ceramic member is configured to increase adhesion between the first polymer layer and second polymer layer.

In another example, the disclosure relates to a method for forming an implantable medical lead configured to at least one of deliver electrical stimulation to a patient or sense electrical activity of the patient, the method comprising forming a first polymer layer; and forming a second polymer layer to form a thin film. The thin film comprises at least one electrode, at least one electrical contact, at least one electrically conductive track extending between the at least one electrode and the at least one electrical contact, the first polymer layer; the second polymer layer, wherein, at a portion of the thin film between the at least one electrode and the at least one electrical contact, the first polymer layer and second polymer layer surround the at least one electrically conductive track; and at least one discrete ceramic member located between the first and second polymer layers at a portion of the thin film between the at least one electrode and the at least one electrical contact, wherein the at least one discrete ceramic member does not surround the at least one conductive track at the portion of the thin film between the at least one electrode and the at least one electrical contact, and wherein the at least one discrete ceramic member is configured to increase adhesion between the first polymer layer and second polymer layer.

In another example, the disclosure relates to a medical device system comprising an implantable medical device; and an implantable medical lead, wherein the implantable medical device is configured to at least one of deliver electrical stimulation to a patient or sense electrical activity of the patient via the implantable medical lead, wherein the implantable lead comprises a thin film including at least one electrode, at least one electrical contact, at least one electrically conductive track extending between the at least one electrode and the at least one electrical contact, a first polymer layer; a second polymer layer, wherein, at a portion of the thin film between the at least one electrode and the at least one electrical contact, the first polymer layer and second polymer layer surround the at least one electrically conductive track; and at least one discrete ceramic member located between the first and second polymer layers at a portion of the thin film between the at least one electrode and the at least one electrical contact, wherein the at least one discrete ceramic member does not surround the at least one conductive track at the portion of the thin film between the at least one electrode and the at least one electrical contact, and wherein the at least one discrete ceramic member is configured to increase adhesion between the first polymer layer and second polymer layer.

The details of one or more examples are set forth in the accompanying drawings and the description below. Other features, objects, and advantages will be apparent from the description and drawings, and from the claims.

DETAILED DESCRIPTION

Electrical stimulation systems are under development with an increased number of electrodes and smaller electrodes (e.g., in order to better control the delivery of electrical stimulation) in a technology based on thin film manufacturing. These systems may include an electrical stimulation lead made from a thin film based on thin film technology, e.g., as described in PCT Application Publication WO 2010/055453 A1, to Harberts et al., entitled "Spiraled Wires in a Deep-Brain Stimulator Probe." In some examples, the electrical stimulation lead may include a multilayer thin film fixed on a carrier core, which provides mechanical strength to the thin film. These leads may have multiple electrode areas and may enhance the precision of stimulation (and/or sensing of electrical signals) to address the appropriate target in the brain and relax the specification of electrode positioning. Meanwhile, undesired side effects due to undesired stimulation of neighboring areas may be minimized. Some example leads that are based on thin film manufacturing may include, e.g., those described by U.S. Pat. No. 7,941,202, to Hetke et al., entitled "Modular Multichannel Microelectrode Array and Methods of Making Same," and U.S. Patent Application Publication No. 2011/0093052, to Anderson et al., and entitled "Neural Interface System," and have been used in research products in animal studies.

In some examples, the multilayer thin film may be configured to define relatively small electrodes (e.g., exposed electrically conductive surfaces) in a distal electrode array of a lead, which may be used, e.g., for DBS. In the distal electrode array, the thin film may include metal electrodes that are electrically coupled to conductive tracks extending along the thin film of the lead to one or more proximal electrical contacts. The electrically conductive tracks may be surrounded in the thin film between the electrodes and electrical contacts by a flexible ceramic insulator to provide integrity and electrical insulation. For reasons of biocompatibility, a biocompatible polymer, such as, e.g., one or more of the polymers sold under the trade name Parylene, may be wrapped around the insulated electrically conductive tracks to surround the insulated electrically conductive tracks within the thin film. The tracks may be surround by forming of a first polymer layer on the tracks over a first side and then forming a second polymer layer on the other side(s) of the tracks such that all side of the tracks are covered by a polymer material between the distal electrode and proximal electrical contact.

However, the level of adhesion of the first polymer layer and second further polymer layer to each other, after being formed, may be unsuitable in some instances. In some examples, the adhesion between the respective polymer layers may even deteriorate when the overall structure is exposed to saline solutions and/or when implanted into a mammalian body, e.g., during animal testing and/or during implantation in a human brain.

It is therefore an object, in some examples of the disclosure, to improve a multilayer structure and its method of manufacturing, in particular in that the overall adhesion of two biocompatible polymer layers may be improved. This object may be solved, in some examples, according to the present disclosure with a multilayer structure and a method of manufacturing a multilayer structure as described in this disclosure.

For example, a lead may include a multilayer structure with an electrically conductive track covered by the combination of a first polymer layer and second polymer layer, where at least a portion of the polymer layers are in contact with each other. The lead may further include at least one discrete ceramic member separate from the electrically conductive tracks and which is located between the first polymer layer and the second polymer layer. By providing at least one discrete ceramic element between the two polymer layers, the adhesion between both layers may be surprisingly improved. In this manner, a lead may be formed with desirable adhesion between the polymer layers via the discrete ceramic member or members. In some examples, the adhesion may even be improved such that the multilayer structure may be exposed to saline solutions and withstand such exposure as may occur when implanted into a mammalian body, e.g., during animal testing or when implanted in a human.

Figure 1:
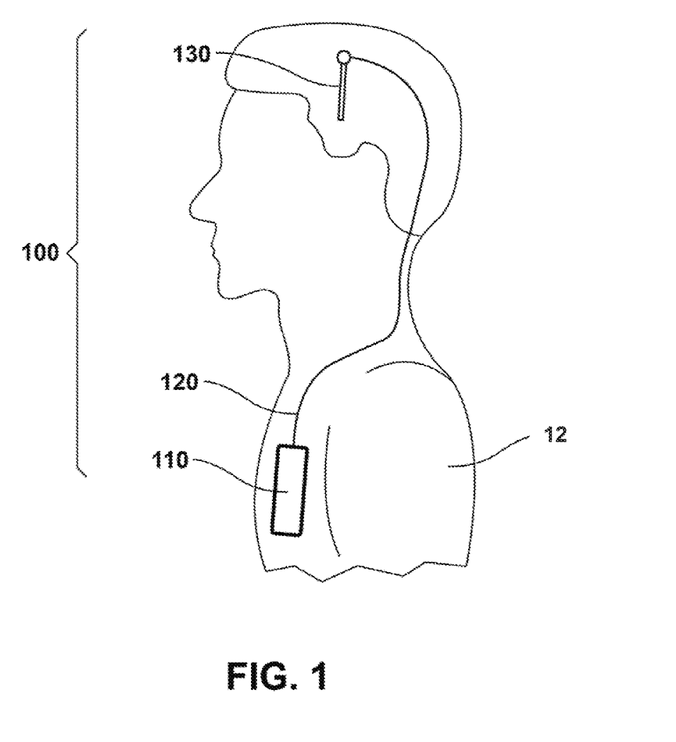
FIG. 1 is a schematic diagram illustrating an example neurostimulation system for delivery of DBS.

FIG. 1 a schematic diagram illustrating an example neurostimulation system 100 for delivery of deep brain stimulation (DBS). As shown, the neurostimulation system 100 may include controller 110 (also referred to as an implantable pulse generator or "IPG") that may be surgically implanted in the chest region of a patient 12, e.g., below the clavicle or in the abdominal region of a patient 12. Controller 110 may be configured to generate and supply the necessary voltage pulses or other suitable type of electrical stimulation for delivery to patient 12 via DBS probe 130. Neurostimulation system 100 may further include a lead extension 120 connected to controller 110 and running subcutaneously to the skull of patient 12, e.g. along the neck, where it terminates in a connector (not shown). The DBS probe 130 may be coupled to the connector of the lead extension 120 and be implanted in the brain tissue of patient 12, e.g., through a burr-hole in the skull.

Figure 2A:
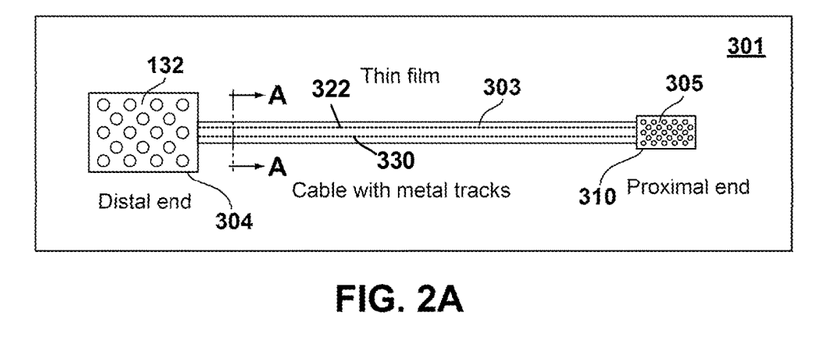
FIGS. 2A-2C are schematic diagrams illustrating various aspects of an example probe of a neurostimulation system for deep brain stimulation (DBS).
Figure 2B:
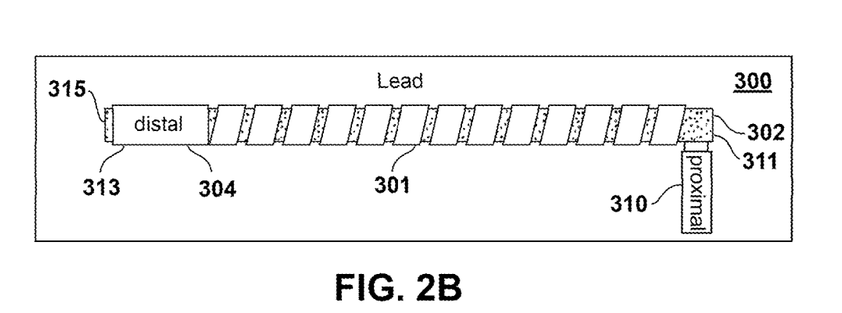
Figure 2C:
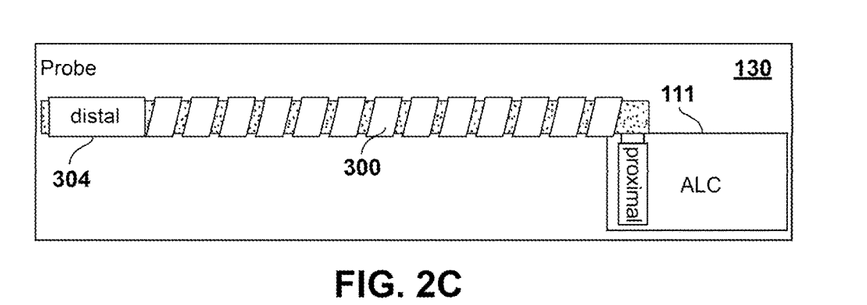

FIGS. 2A-2C are schematic diagrams illustrating an example architecture for DBS probe 130 and other components of system 100. As shown, DBS probe 130 includes DBS lead 300 and active lead can (ALC) 111. Lead 300 comprises thin film 301 wrapped around carrier core 302. Carrier core 302 may provide the mechanical configuration of DBS lead 300 and thin film 301. Thin film 301 may include at least one electrically conductive layer (not shown), preferably made of a biocompatible material. Thin film 301 may be wrapped about carrier core 302 and further processed to form lead 300. As will be described further below, thin film 301 for lead 300 may be formed by a multilayer thin film product including distal end 304, cable 303 with electrically conductive tracks (e.g., metal tracks) and proximal end 310.

Carrier core 302 may have any suitable configuration. In some examples, carrier core 302 may be an elongated member having a circular cross-section, although other cross-sections are contemplated, such as, e.g., square or hexagonal. Carrier core 302 may be a solid member or have a hollow core. In some examples, it is preferred that carrier core 302 be relatively stiff during implantation but able to flex or bend to some degree after implantation. The hollow core may allow for the insertion of a stiffening member such as a stylet into the hollow core, e.g., during implantation of lead 300. Carrier core 302 may be configured to not substantially shrink, stretch, or compress during and/or after implantation.

In some examples, carrier core 302 should be flexible and have a good rotational torque transfer, e.g., in instances of permanent (chronic) implant of lead 300. Some acute applications may have a different set of preferences. For instance, in acute implantation, no burr-hole devise may be used and flexibility and limited compressibility are of less concern.

Carrier core 302 may be formed of any suitable material including silicone, titanium, and/or polyether ether ketone (PEEK) based materials. For the mechanical requirements as mentioned above, other polymers can be more useful e.g. bionate. In addition, metal tubes (e.g., laser machined to bendable chains) may be used. In acute applications, a solid metal may be used for carrier core 302. In acute application, there may not be a need for carrier core 302 to be hollow or flexible. In chronic applications, carrier core 302 is implanted with a stiffener inside. After implantation, the stiffener may be removed.

Distal portion of lead 300 may have a diameter between about 0.5 millimeters (mm) and about 3 mm diameter, e.g., about 1.3 mm. The diameter of lead 300 may be defined by the diameter of carrier core 302 in combination with the thickness of thin film 301 and any coating applied over carrier core 302 and/or thin film 301. The proximal portion of lead 300 (the portion adjacent to ALC 111) may have a diameter between about 0.5 mm and about 4 mm diameter. The length of lead 300 may be about 10 centimeters (cm) to about 20 cm, e.g., about 15 cm, and may vary based on the particular application, e.g., acute versus chronic implantation. Other dimensions than those examples described herein are contemplated.

As shown, proximal end 310 of thin film 301 may be arranged at proximal end 311 of lead 300. Proximal end 310 of thin film 301 may be connected to the active lead can 111. For example, active lead can 111 may be electrically coupled to array of electrodes 132 on distal end 304 of thin film 301, which is arranged at distal end 313 and next to distal tip 315 of DBS lead 300. Active lead can 111 may include the switch matrix of DBS steering electronics. Distal end 304 comprises an array of electrodes 132 for the brain stimulation. Proximal end 310 comprises electrical interconnect contacts 305 for each electrically conductive track in the cable 303. Cable 303 comprises a plurality of electrically conductive tracks to connect each distal electrode 132 to a respective designated proximal contact 305. That is, each one of the distal electrodes 132 may be electrically coupled to a respectively different conductive track in cable 303, which may, in turn, be coupled to a respectively different one of proximal contacts 305. This allows each one of the distal electrodes to be programmed and used independently of the other electrodes for sensing and/or stimulation.

In one example, each of the electrodes may be coupled to a different respective independently-controlled current or voltage source. Alternatively, some electrodes can be coupled to the same current or voltage source. Stimulation can be delivered using a selected combination of the electrodes, allowing the field of the stimulation, and thus the area of tissue that is activated, to be shifted, or "steered", around the circumference of the lead to more accurately deliver stimulation while avoiding side effects.

As described above, lead 300 may be formed by winding thin film 301 around carrier core 302. Micromachining technology such as thin film technologies to manufacture thin film 301 may enable the realization of smaller electrodes. Again, the multilayer lead structure may be used in medical devices like active implantable devices such as, e.g., implantable neurostimulation devices. For example, lead 300 may be employed with an implantable neurostimulation device as part of a deep brain stimulation system to deliver DBS therapy for treatment of any number of neurological disorders or diseases. Examples of such neurological disorders may include movement disorders such as Parkinson's disease, tremor, and spasticity, epilepsy, depression, dementia, obsessive-compulsive disorder, Alzheimer's disease, migraines, and obesity.

One or more leads such as lead 300 may further be used as part of stimulation system to treat a variety of other symptoms or conditions, such as chronic pain, urinary or fecal incontinence, sexual dysfunction, or gastroparesis, cardiac arrhythmia and cardiac fibrillation. In these latter examples, lead 300 may be positioned to deliver stimulation at a variety of tissue sites outside the brain including the spinal cord, the sacral nerve, pelvic nerves, peripheral nerves, the heart, the vagal nerves, the tibial nerves, or the gastrointestinal tract of a patient. Thus while lead 300 is sometimes referred to herein as a "DBS lead", it will be understood that this lead can be used for other therapies besides DBS therapies and the use of this lead for DBS therapies is merely one example.

Thin film structures may provide an advantage in that a relatively small structure can be built with this technology. A thin film may be a layer or multilayer structure of material ranging from fractions of a nanometer (monolayer) to several micrometers in thickness. Electronic semiconductor devices and optical coatings are applications benefiting from thin-film construction. Thin film technology and thin film manufacturing processes may allow the manufacturing of leads for medical purposes such as neurostimulation leads like, e.g., deep brain stimulation leads with diameters of less than 2 mm, for example 0.75 mm to 1.50 mm and a plurality of electrodes (e.g., approximately 10 electrodes or greater, preferably approximately 20 electrodes or greater, preferably approximately 40 electrodes or greater).

Figure 3:
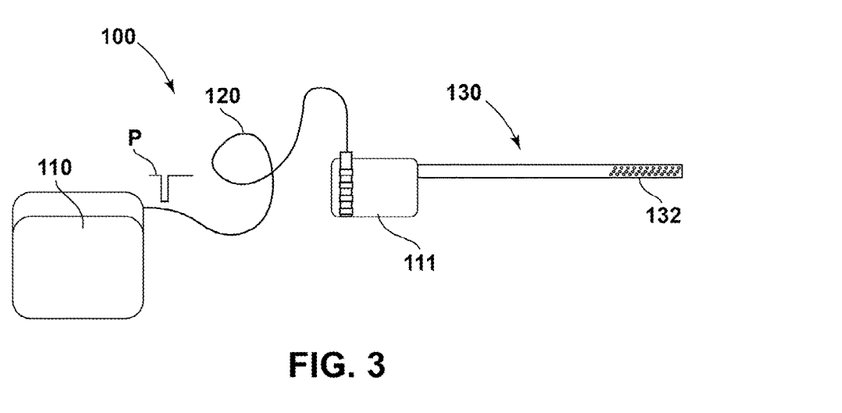
FIG. 3 is a schematic diagram illustrating the example probe system of FIG. 1.

FIG. 3 shows schematically and in greater detail an embodiment of a system 100 for brain applications, here for neurostimulation and/or neurorecording as a deep brain stimulation system 100 as shown in FIGS. 1 and 2A-2C. System 100 comprises at least one probe 130 for brain applications with stimulation and/or recording/sensing electrodes 132, wherein, e.g., an array of forty total electrodes 132 may be located on an outer body surface at the distal end of the probe 130. By way of the lead extension 120, electrical stimulation, such as, e.g., pulses P, supplied by controller 110 may be transmitted to active lead can 111. The electrical stimulation may be transmitted from active can lead 111 to array of electrodes 132 to deliver the electrical stimulation to a target tissue in the brain of patient 12.

In some example systems, DBS lead 300 includes four 1.5 mm-wide cylindrical electrodes at the distal end spaced by about 0.5 mm or about 1.5 mm apart from one another. Cylindrical electrodes are sometimes referred to as ring electrodes. The diameter of lead 300 may be about 1.27 mm and the conductive material (e.g., metal) used for electrodes 132 and the interconnect wires (not shown) may be an alloy of platinum and iridium. The coiled interconnect wires may be insulated individually by fluoropolymer coating and protected in an 80 micron urethane tubing. With such an example electrode design, the current distribution may emanate uniformly around the circumference of the electrode, which leads to electrical stimulation of all areas surrounding the electrode.

In other examples, the electrodes may form an array of electrodes with a complex electrode array geometry that is capable of producing shaped electrical fields. An example of a complex electrode array geometry may include an array of electrodes positioned at different axial positions along the length of a medical lead, as well as at different angular positions about the periphery, for example, circumference, of the medical lead. The complex electrode array geometry may include multiple electrodes (e.g., partial ring or segmented electrodes) around the perimeter of each medical lead 20. In other examples, the complex electrode array geometry may include electrode pads distributed axially and circumferentially about the medical lead. In either case, by having electrodes at different axial and angular positions, electrical stimulation may be directed in a specific direction from probe 130 to enhance therapy efficacy and reduce possible adverse side effects from stimulating a large volume of tissue. In some examples, the array of electrodes may be combined with one or more ring electrodes on probe 130.

Figure 7:
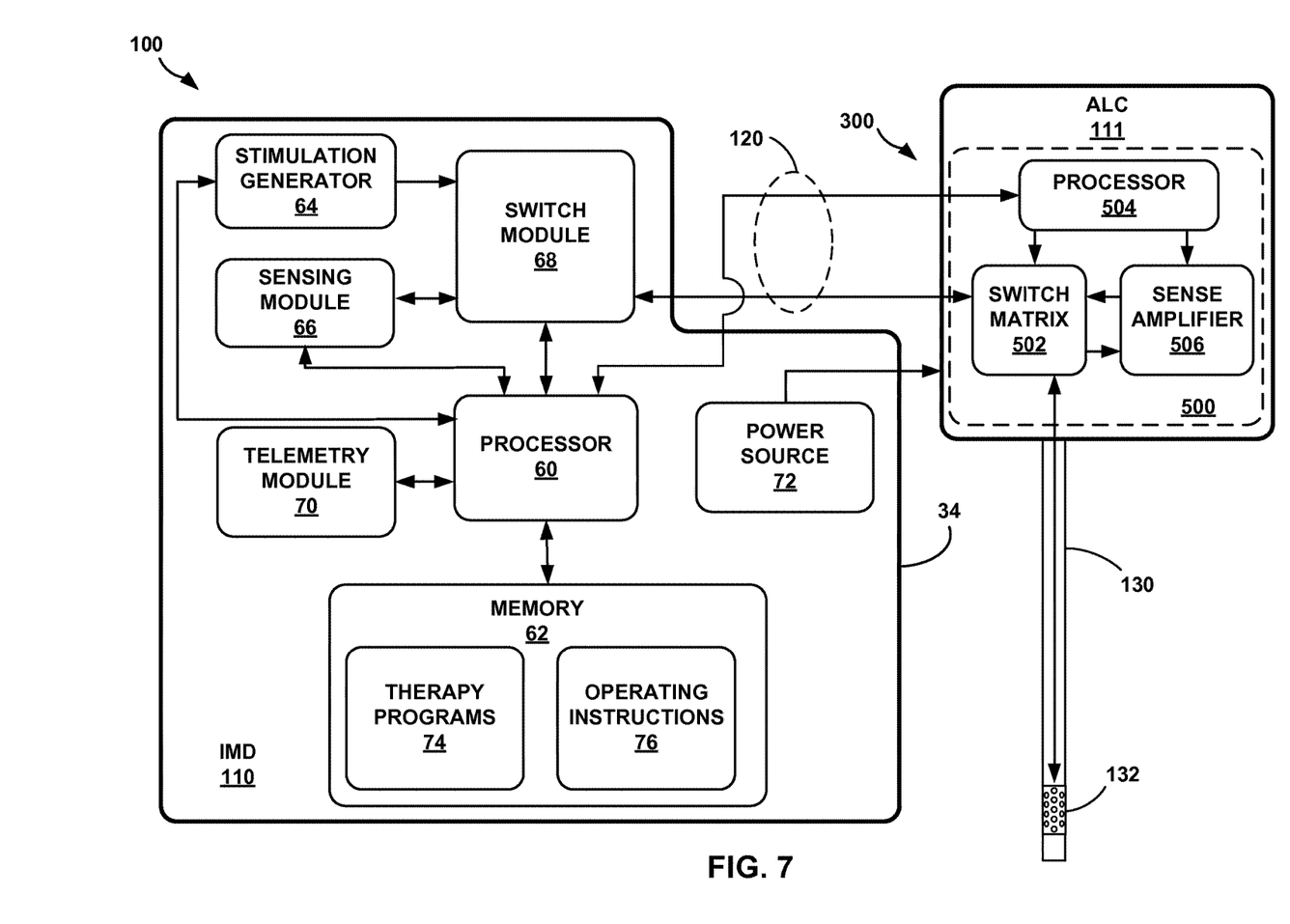
FIG. 7 is a functional block diagram illustrating components of an example medical device system including an implantable medical device and a active lead can (ALC) with a switch matrix to direct signals from the implantable medical device to different electrodes.

FIG. 7 is functional block diagram illustrating components of an example therapy system 100 including IMD 110 and ALC 111. In the example shown in FIG. 7, IMD 110 includes processor 60, memory 62, stimulation generator 64, sensing module 66, switch module 68, telemetry module 70, and power source 72. Memory 62, as well as other memories described herein, may include any volatile or non-volatile media, such as a random access memory (RAM), read only memory (ROM), non-volatile RAM (NVRAM), electrically erasable programmable ROM (EEPROM), flash memory, and the like. Memory 62 may store computer-readable instructions that, when executed by processor 60, cause IMD 110 to perform various functions described herein.

In the example shown in FIG. 2, memory 62 stores therapy programs 74 and operating instructions 76, for example, in separate memories within memory 62 or separate areas within memory 62. Each stored therapy program 74 defines a particular program of therapy in terms of respective values for electrical stimulation parameters, such as an electrode combination, current or voltage amplitude, and, if stimulation generator 64 generates and delivers stimulation pulses, the therapy programs may define values for a pulse width, and pulse rate of a stimulation signal. The stimulation signals delivered by IMD 110 may be of any form, such as stimulation pulses, continuous-wave signals (e.g., sine waves), or the like. Operating instructions 76 guide general operation of IMD 110 under control of processor 60, and may include instructions for monitoring brain signals within one or more brain regions via electrodes 132 and delivering electrical stimulation therapy to patient 12.

Stimulation generator 64, under the control of processor 60, generates stimulation signals for delivery to patient 12 via selected combinations of electrodes 132. In some examples, stimulation generator 64 generates and delivers stimulation signals to one or more target regions of brain 28 (FIG. 1), via a select combination of electrodes 132, based on one or more stored therapy programs 74. Processor 60 selects the combination of electrodes 132 with control signals to processor 504 of ALC 111. In turn, processor 504 of ALC 111 selectively activates active switch matrix 504 to direct the stimulation signals received from stimulation generator 64 to the selected electrodes 132. The stimulation parameter values and target tissue sites within brain 28 for stimulation signals or other types of therapy may depend on the patient condition for which therapy system 100 is implemented to manage.

The processors described in this disclosure, including processor 60 and processor 504, may include one or more digital signal processors (DSPs), general-purpose microprocessors, application specific integrated circuits (ASICs), field programmable logic arrays (FPGAs), or other equivalent integrated or discrete logic circuitry, or combinations thereof. The functions attributed to processors described herein may be provided by a hardware device and embodied as software, firmware, hardware, or any combination thereof. Processor 60 is configured to control stimulation generator 64 according to therapy programs 74 stored by memory 62 to apply particular stimulation parameter values specified by one or more therapy programs.

Processor 60 may control switch module 68 to select stimulation generator 64 or sensing module 66. In turn, processor 60 directs processor 504 of electronic module 500 to apply the stimulation signals generated by stimulation generator 64 to selected combinations of electrodes 132, or to sense signals from selected combinations of electrodes 132 via sense amplifier 506 of electronic module 500. In particular, active switch matrix 502 of electronic module 500 may couple stimulation signals to selected conducting tracks within probe 130, which, in turn, deliver the stimulation signals to selected electrodes 132. Hence, although there may be many, for example, 40, electrodes, active switch matrix 502 may select a subset of one, two or more electrodes for delivery of stimulation pulses. Active switch matrix 502 may be a switch array, an array of one or more transistors such as Field-Effect Transistors (FETs), switch matrix, multiplexer and/or demultiplexer, or any other type of switching module configured to selectively couple stimulation energy to selected electrodes 132 and to selectively sense bioelectrical brain signals with selected electrodes 132. Hence, stimulation generator 64 is coupled to electrodes 132 via switch module 68, conductors within cable 120 between IMD 110 and ALC 111, active switch matrix 502, and conducting tracks within probe 130. Additionally, the logic path between stimulation generator and electrodes 132 may include one or more discrete components such as capacitors, resistors, logic gates, transistors, and the like. Thus, it will be understood that when reference is made to coupling of stimulation generator 64 or other components of IMD 110 to electrodes 132, this refers to the enabling of a logic path between the logic components so that signals may be transferred there between, and is not intended to necessarily require a direct electrical coupling of the components.

In some examples, IMD 110 does not include switch module 68 and all switching functions may be performed by active switch matrix 502. For example, IMD 110 may include multiple sources of stimulation energy (e.g., current sources). Additionally or alternatively, a stimulation generator similar to stimulation generator 64 may reside within ALC (not shown) and may generate the stimulation pulses that are routed to electrodes 132 via active switch matrix 502. In such cases, the stimulation generator within the ALC may receive power from power source 72 and may receive control signals from stimulation generator 64 or other logic of IMD 110. The stimulation generator in ALC may be provided in addition to, or instead of, stimulation generator 64 of IMD 110. Thus, electronics for driving probe 130 and electrodes 132 of lead may reside in IMD 110, ALC 111, or some combination thereof. Stimulation generator 64 and/or a stimulation generator residing within ALC 111 may be a single channel or multi-channel stimulation generator. In particular, stimulation generator 64 may be capable of delivering a single stimulation pulse, multiple stimulation pulses or continuous signal at a given time via a single electrode combination or multiple stimulation pulses at a given time via multiple electrode combinations. In some examples, however, stimulation generator 64 and active switch matrix 502 may be configured to deliver multiple channels of stimulation on a time-interleaved basis. For example, active switch matrix 502 may serve to time divide the output of stimulation generator 64 across different electrode combinations at different times to deliver multiple programs or channels of stimulation energy to patient 12. In another example, system 100 may not include ALC 111 between IMD 110 and probe 130. In such an example, the entire functionality attributed to the combination of IMD 110 and ALC 11 may be performed by components of IMD 110.

Sensing module 66, under the control of processor 60, is configured to sense bioelectrical brain signals of patient 12 via active switch matrix 502, sense amplifier 506, and a selected subset of electrodes 132 or with one or more electrodes 132 and at least a portion of a conductive outer housing 34 of IMD 110, at least a portion of a conductive outer housing of ALC 111, an electrode on outer housing 34 of IMD 110, an electrode on an outer housing of ALC 111, or another reference. Processor 60 may control switch module 68 and/or switch matrix 502 to electrically connect sensing module 66 to selected electrodes 132 via active switch matrix 502 and sense amplifier 506 of ALC 111. In this way, sensing module 66 may selectively sense bioelectrical brain signals with different combinations of electrodes 132.

Telemetry module 70 is configured to support wireless communication between IMD 110 and an external programmer (not shown) or another computing device under the control of processor 60. Processor 60 of IMD 110 may receive, as updates to programs, values for various stimulation parameters from an external programmer via telemetry module 70. The updates to the therapy programs may be stored within therapy programs 74 portion of memory 62. Telemetry module 70 in IMD 110, as well as telemetry modules in other devices and systems described herein, such as an external programmer, may accomplish communication by RF communication techniques. In addition, telemetry module 70 may communicate with an external medical device programmer via proximal inductive interaction of IMD 110 with the programmer. Accordingly, telemetry module 70 may send and receive information to/from an external programmer on a continuous basis, at periodic intervals, or upon request from IMD 110 or the programmer.

Power source 72 delivers operating power to various components of IMD 110. Power source 72 may include a small rechargeable or non-rechargeable battery and a power generation circuit to produce the operating power. Recharging may be accomplished through proximal inductive interaction between an external charger and an inductive charging coil within IMD 110. In some examples, power requirements may be small enough to allow IMD 110 to utilize patient motion and implement a kinetic energy-scavenging device to trickle charge a rechargeable battery. In other examples, traditional batteries may be used for a limited period of time.

Figure 4:
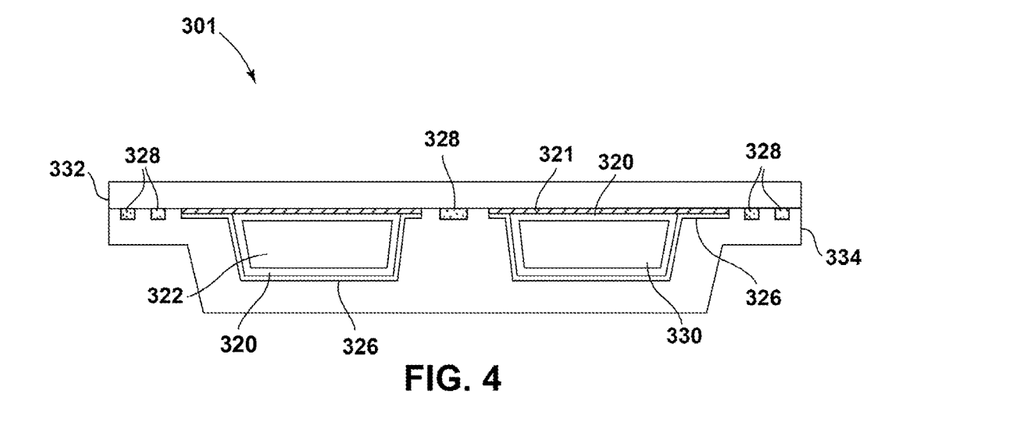
FIG. 4 is a conceptual diagram illustrating an example cross section of a multilayer structure according to the present disclosure.

FIG. 4 is a conceptual diagram illustrating a cross-sectional view of thin film 301 of lead 300 along A-A indicated in FIG. 2A. As shown, thin film 301 includes first electrically conductive track 322 and second electrically conductive track 330 surround by the combination of first polymer layer 332 and second polymer layer 334 at portion of thin film 301 between electrodes 132 and contacts 305. Each of first track 322 and second track 330 may extend along the length of thin film 301, and may be electrically coupled to ALC 111 (e.g., via proximal contacts 305) and a respective electrode of array of electrodes 132. For ease of illustration, lead 301 is shown to only include two electrically conductive tracks extending within the structure of thin film 301. However, lead 301 may include any suitable number of electrically conductive tracks, e.g., where each conductive track may correspond to an individual electrode in array of electrodes 132. Accordingly, in some examples, for N electrodes, there may be N corresponding electrically conductive tracks.

First and second electrically conductive tracks 322 and 330 may be formed of a metal to define a metal track. In some examples, tracks 322 and 330 are both formed of gold (Au) and/or platinum (Pt). As shown, in some examples, tracks 322 may also be individually surrounded by a layer of platinum (Pt) 320, e.g., in the case of tracks 322 and 330 being formed of Au. In some examples, combinations of copper (Cu) and titanium (Ti) may be employed or a Pt/Ti/Cu structure may be used. These metal layers may each have a thickness in a range between a few nanometers (nm) to a few microns although other thicknesses are contemplated.

In some examples, these Pt or Pt-encased Au tracks 322 and 330 or other type of electrically conductive tracks may further be individually surrounded by ceramic in the combination of first ceramic layer 321 and second ceramic layer 326. By this, the adhesion between polymer layers 332 and 334 and the metal tracks 322 and 330 may be improved. For example, the adhesion of ceramic materials such as siliconnitride (SiN) and/or siliconoxide (SiOx) to a metal like platinum, e.g., may be made with relatively high adhesion strength. The adhesion at this interface may be further enhanced by adhesion layers like titanium layers between the metal layer like, e.g., the platinum layer, and the ceramic material. In some examples, first ceramic layer 321 and second ceramic layer 326 comprise at least one of SiN, SiOx, Si-Carbide, alumina, or oxynitride. These materials are biocompatible materials and thus may be advantageously used for medical purposes. First ceramic layer 321 and second ceramic layer 326 may have a thickness between approximately 100 nanometers to several microns although other thicknesses are contemplated.

First and second polymer layers 332 and 334 surround all sides of conductive tracks 322 and 330 in the portion of thin film 301 at cross section A-A. First and second polymer layer 332 and 334 may surround tracks 322 and 330 along the entire axial length of thin film 301 from the respective individual electrode and individual contact that each track extends between to conductive electrical signals. One advantage achieved by this structure may be that the polymer layer provides a soft coating which is better accepted by surrounding tissue when, e.g., implanted into a mammalian body such as a human body.

First and second polymer layers 332 and 334 may be formed of any suitable polymer material. In some examples, first and second polymer layers 332 and 334 may comprise, consist, or consist essentially of a medical grade polymer. For example, the medical polymer may be at least one of a polymer referred to under the trade name of Parylene (e.g., Parylene-C), SU-8, silicone, polyimide, or polyurethane. These polymers may be used when the polymer might be exposed during use to tissue, e.g., when the multilayer structure is implanted into a mammalian body. First and second polymer layers 332 and 334 may be up to tens of microns in thickness or more although other thicknesses are contemplated.

Parylene is a name for a variety of chemical vapor deposited polyp-xylylene) polymers used, e.g., as ion barriers including ions that are dissolved in water. In some examples, a Parylene polymer is a biocompatible material. Polyurethane (PUR and PU) is a polymer composed of a chain of organic units joined by carbamate (urethane) links. While most polyurethanes are thermosetting polymers that do not melt when heated, thermoplastic polyurethanes are also available. Polyurethane polymers may be formed by reacting a di- or poly-isocyanate with a polyol. Both the isocyanates and polyols used to make polyurethanes contain on average two or more functional groups per molecule. Medical grade polyurethanes are available and may be used. Both Parylene polymers and PU can be structured to shape by standard photolithography and etch processes. A photoresist may be used to photodefine the structures.

SU-8 and also polyimide (sometimes abbreviated PI) may have direct photoimaging properties and no separate photoresist layer is needed to structure these polymer layers. SU-8 may be used as an epoxy-based negative photoresist. It is a very viscous polymer that can be spun or spread over a thickness ranging from, e.g., greater than approximately 1 micrometer up to approximately 300 micrometer, and still be processed with standard lithography. It may be used to pattern high aspect ratio (e.g., greater than 20) structures. Its maximum absorption is for ultraviolet light with a wavelength of 365 nm (it may not be practical to expose SU-8 with g-line ultraviolet light). When exposed, SU-8's long molecular chains cross-link causing the solidification of the material. SU-8 series photoresists may use gamma butyrolactone as the primary solvent.

In some examples, the silicone may be a medical grade silicone. Medical grade silicones are silicones tested for biocompatibility and are appropriate to be used for medical applications. In the United States, the Food and Drug Administration (FDA) regulates materials implanted into the body. Medical grade silicones are generally grouped into three categories: non-implantable, short-term implantable, and long-term implantable. Materials approved as USP Class V and VI can be considered medical grade. Most medical grade silicones are at least Class VI certified. More precisely called polymerized siloxanes or polysiloxanes, silicones may be mixed inorganic-organic polymers with the chemical formula [R2SiO]n, where R is an organic group such as methyl, ethyl, or phenyl. These materials include an inorganic silicon-oxygen backbone ( . . . —Si—O—Si—O—Si—O— . . . ) with organic side groups attached to the silicon atoms, which are four-coordinate.

Polyimide (sometimes abbreviated PI) is a polymer of imide monomers. Polyimides have been in mass production since 1955. Example monomers include pyromellitic dianhydride and 4,4'-oxydianiline. Biocompatible polyimides may be available and may be used. For implants comprising thin film elements, such as, e.g., leads for medical systems like neurostimulation systems or more specifically deep brain stimulation systems, parylene may be one of the preferred materials to surround, e.g., metal lines or tracks or traces such as conductive tracks 322 and 330. This may be accomplished by forming a first layer over a first side of the metal lines and forming a second layer over the first layer and metal lines to cover the remaining side of the metal lines not covered by the first layer.

As shown in FIG. 4, first polymer layer 332 and second polymer layer 334 may be in direct contact with each other in the multilayer configuration of thin film 301. As described above, in some instances, the adhesion of first polymer layer 332 and second polymer layer 334 to each other (e.g., adhesion of a Parylene polymer layer to another Parylene polymer layer) may be relatively low. The adhesion of first polymer layer 332 and second polymer layer 334 may even deteriorate when exposed to saline solutions and when implanted into a mammalian body.

Accordingly, as shown in FIG. 4, thin film 301 may also include discrete ceramic members 328 located between first polymer layer 332 and second polymer layer 334. Discrete ceramic members 328 may be in direct contact with first polymer layer 332 and also in direct contact with second polymer layer 334. Unlike that of ceramic layers 326, 321, discrete ceramic members 328 do not surround first track 322 or second track 330 as shown in FIG. 4. Each individual discrete ceramic member 328 may increase the adhesion between first polymer layer 332 and second polymer layer 334. For example, first polymer layer 332 and second polymer layer 324 may each adhere better to discrete ceramic member 328 compared to the adherence between first and second polymer layers 332, 334 when in direct contact with each other. By including discrete ceramic members 328 between first and second polymer layers 332, 334, the area over which first polymer layer 332 is in direct contact with second polymer layer 334 is reduced while the area over which first polymer layer 332 is in indirect contact with second polymer layer 334 via a ceramic material is increased. As such, the overall adhesion of first polymer layer 332 and second polymer layer 334 is increased, e.g., compared to a configuration like that of FIG. 4 but without including discrete ceramic members 328, i.e., a configuration like FIG. 4 but with discrete ceramic members 328 omitted.

Figure 5:
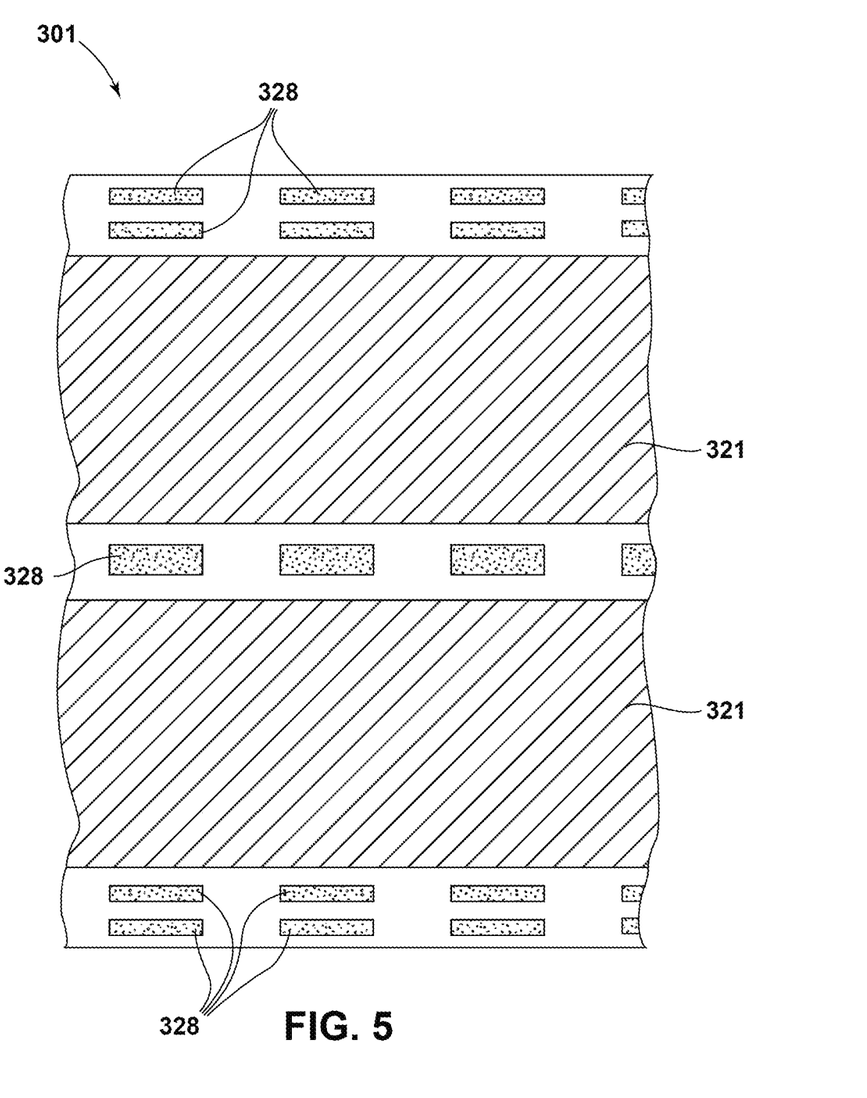
FIG. 5 is a conceptual diagram illustrating a top view of the multilayer structure of FIG. 4 with the top polymer layer removed.

FIG. 5 is a schematic diagram of thin film 301 of lead illustrating a top view of a portion of thin film 301 corresponding to the cross-section shown in FIG. 4. To illustrate the configuration of discrete ceramic members 328, thin film 301 is shown in FIG. 5 with first polymer layer 332 removed. As shown, each individual discrete ceramic member 328 may be a discontinuous "island" of ceramic material located between first polymer layer 332 and second polymer layer 334. Unlike that of first and second electrically conductive tracks 322, 330, discrete ceramic members 328 may not extend along the length of thin film 301. Rather, a plurality of separate ceramic members 328 may be positioned along the length of thin film 301, forming a discontinuous series of ceramic members in the thin film, e.g., between the distal electrodes 132 and proximal contacts 305. Additionally, in some examples, discrete ceramic members 328 are surrounded first polymer layer 332 and second polymer layer 334, and do not directly contact electrically conductive tracks 322, 330, ceramic layers 321, 326, and/or Pt layer 320.

Again, it has been found that, in some examples, the inclusion of discrete ceramic members 328 (or ceramic "islands") in the manner described herein between first polymer layer 332 and second polymer layer 334 is sufficient to improve the overall adhesion of the first and second polymer layers 332, 334 in thin film 30. Due in part to the discontinuous nature of discrete ceramic members 328, multilayer thin film 301 may also maintain its flexibility, although the area of polymer to polymer direct contact is minimized. For example, the ceramic element, which bond the polymer layers to each other, and the metal track do not contact each other. As a result, the multilayer structure may remain flexible, e.g., due to the fact that discrete ceramic elements 328 and electrically conductive tracks 322, 330, and layers surrounding those tracks, do not contact each other but are instead separated by the polymer material of first and second polymer layers 332, 334. For example, the polymer portion between discrete ceramic elements 328 and electrically conductive tracks 322, 330, may allow bending of thin film 301 to a certain extent.

Discrete ceramic members 328 may be formed of any suitable ceramic material. For example, similar to that of ceramic layer 321, discrete ceramic members 328 may comprise, consist of, or consist essentially of at least one of SiN, SiOx, Si-Carbide, alumina, or oxynitride. These example ceramic materials may exhibit good biocompatible properties when used in implants. Furthermore, the adhesion to a polymer of these ceramics is good. However, other example ceramics are contemplated, particularly those that exhibit the above properties. Discrete ceramic members 328 may have substantially the same composition of ceramic layer 321 or may have a different composition than ceramic layer 321. Furthermore, each individual discrete ceramic member 328 in thin film 301 may have substantially the same composition as each other or the composition may vary. Each individual ceramic member 328 may be formed of the same ceramic material or different ceramic materials.

Discrete ceramic members 328 may be any suitable shape and size. In some examples, discrete ceramic members 328 may be ceramic "dots," e.g., in the shape of a cylinder. As another example, as shown in FIG. 5, discrete ceramic members 328 may have a rectangular shape when viewed from above. The spacing between individual discrete ceramic members 328 may be selected to provide for a desired level of adhesion between first polymer layer 332 and second polymer layer 334 in thin film 301 while also providing for desired flexibility of thin film 301. For example, the distance between individual discrete ceramic members 328 may be less than or equal to approximately three times the diameter of circular discrete ceramic members 328 or width of rectangular discrete ceramic members 328. Furthermore, any two adjacent ones of the ceramic members 328 may be spaced apart at a predetermined constant interval that is the same for all such pairs of the ceramic members, or the intervals between adjacent pairs of ceramic members 328 may vary.

In some examples, the adhesion of first and second polymer layers 332, 334 to discrete ceramic members 328 and/or ceramic layer 321 may be further improved by using an appropriate adhesion promoter. In particular, this is especially done prior to the deposition of a polymer material forming the layers on to discrete ceramic members 328 and/or ceramic layer 321, as will be described below.

Any suitable adhesion promoter may be used. In some examples, adhesions promoters including organosilanes (e.g., A714 adhesion promoter) may be used. In some examples, the adhesion promoter may include one organic substituent and three hydrolyzable substituents. The organic substitute may bond well to organic surfaces and the hydrolyzable substituents may bond well to inorganic surfaces. As such, the adhesion promoter may form an adhesive bridge between materials that would, otherwise not adhere.

Figure 6:
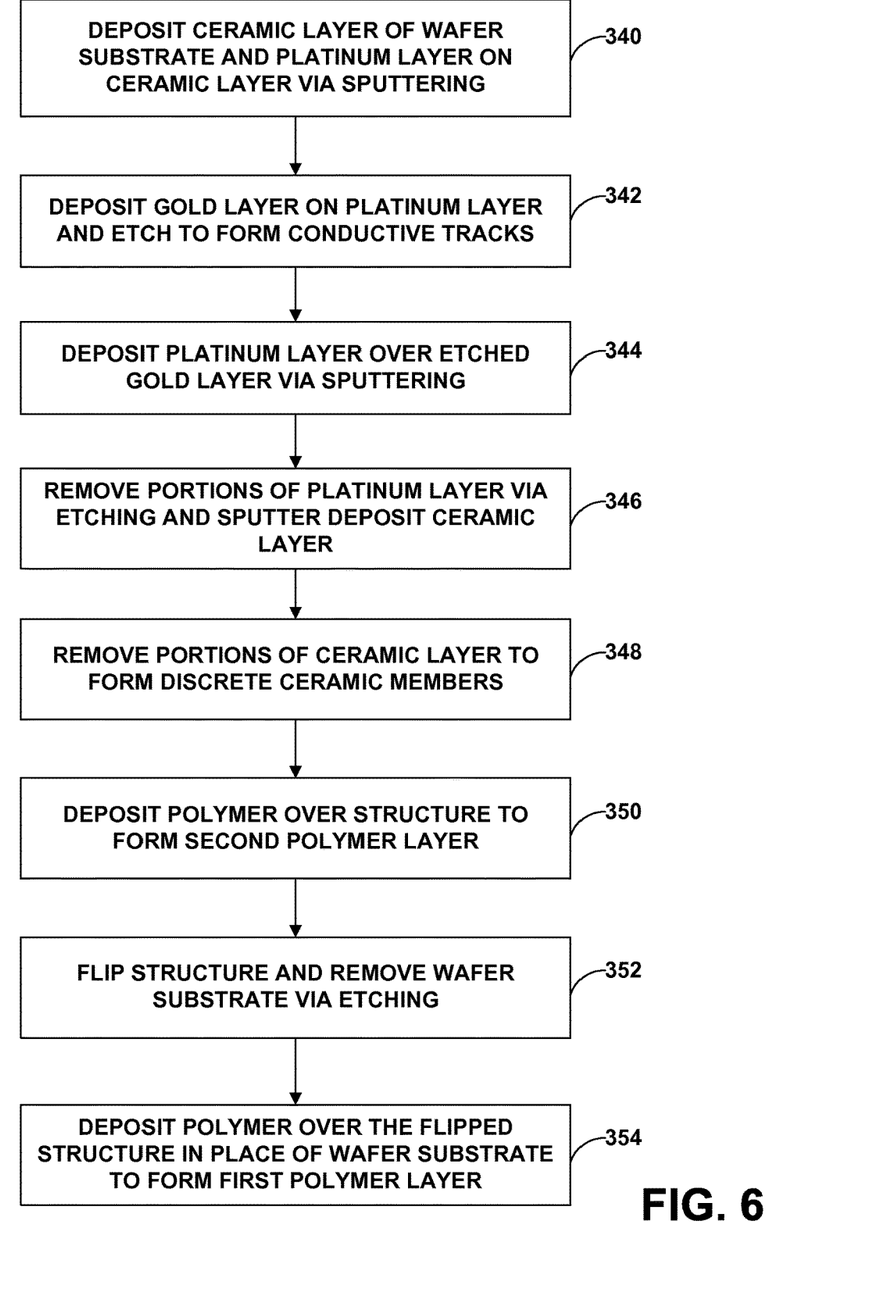
FIG. 6 is a flow diagram illustrating an example technique for forming a multilayer lead according to the present disclosure.

FIG. 6 is a flow diagram illustrating an example technique for forming a multilayer thin film 301 of lead 300 using a thin film deposition process. However, any suitable technique, including thin film deposition, may be employed to form the multi-layer structure described herein to include discrete ceramic members 328 between first and second ceramic layers 332, 334.

As shown in FIG. 6, a ceramic layer (which will later define first ceramic layer 321 and discrete ceramic elements 328) may be sputter deposited on a wafer substrate (e.g., silicon wafer or other suitable wafer substrate), followed by the sputter deposition of a platinum layer (which will later define a portion of platinum layer 320) over the ceramic layer (340). A gold layer may be formed by deposition on the platinum layer, and the gold layer may be subsequently etched to form trapezoidal first and second tracks 322, 330 on the Pt layer (342).

A Pt layer is then sputter deposited on the top and side wall of gold track 322, 330 to encase the gold tracks 322, 330 with Pt in combination with the first formed Pt layer (344). A portion of the Pt layer between tracks 322, 330 is removed via etching to form Au-metal tracks 322, 330 surrounded by Pt layer 320, followed by the sputter deposition of another ceramic layer (corresponding to second ceramic layer 326) (346). Subsequently, portions of the deposited ceramic layers are masked to remove selected portions of the ceramic layers between gold tracks 322, 330 as well as outside each of gold tracks 322, 330 to form discrete ceramic members 328 separate from gold track 322, 330 in the configuration shown in FIGS. 4 and 5 (348). In FIG. 4, first and second ceramic layers 321, 326 may described as a single ceramic layer that surround tracks 322 and 330 individually.

In some examples, after the selected portions of the ceramic have been removed to form discrete ceramic members 328, first ceramic layer 321, and second ceramic layer 326 an appropriate adhesion promoter may be applied to second ceramic layer 326 and discrete ceramic members 328. The adhesion promoter may be applied to the ceramic surface just prior to polymer deposition. The application may be done either from a liquid phase, e.g. by spin casting, or, alternatively, a gas phase application. In some examples, parylene deposition tools are equipped to perform gas phase adhesion promoter application just prior to parylene deposition. The process may be performed without opening the tool between the steps and, as such, avoids air exposure of the treated surface. This integrated approach provides desirable control on the quality of the bond.

Subsequently, a polymer material may be deposited on the remaining structure to form second polymer layer 334 (350). The overall structure may then be flipped, attached to a carrier substrate, and then the wafer substrate may be removed by etching (352). A polymer material may then be deposited on the surface previously occupied by the wafer substrate to form first polymer layer 332 (354). The resulting multilayer structure may have a configuration such as that shown in FIGS. 4 and 5.

In some examples, the present disclosure relates to a method of manufacturing a multilayer structure, such as, e.g., thin film 301, the method comprising placing at least one first polymer layer on a first side of at least one discrete ceramic member; and placing at least one second polymer layer on a second side of the ceramic element. In one example, the ceramic element and the at least one first polymer layer are flipped and sealed on a carrier wafer before the at least one second polymer layer is placed on the second side of the ceramic element. By turning the structure, the substrate may be removed, e.g., by etching, and then the second polymer layer may be provided.

In some examples, by turning/flipping discrete ceramic members 328 and second polymer layer 334, the manufacturing process may be enhanced since the losses of the manufacturing process are minimized, e.g., as compared to removing the discrete ceramic members 328 and second polymer layer 334 from the substrate and attempting to precisely position the discrete ceramic members 328 and second polymer layer 334 for further processing. More parts may be produced without defect since, e.g., discrete ceramic members 328 and metal tracks 322, 330 are not removed from a substrate during the process. In some examples, discrete ceramic members 328 may be provided together with at least one of metal tracks 322, 330, and first polymer layer 332 and second polymer layer 330 are placed thereafter.

As will be apparent from the above description, e.g., with reference to FIGS. 4 and 5, multilayer thin film 301 comprises a first polymer layer 332 and a second polymer layer 334, and at least one discrete ceramic member 328, and in some examples a plurality of discrete ceramic members, located between first polymer layer 332 and second polymer layer 334. The first and the second polymer layers 332, 334 may be directly attached to each other in the sections between ceramic members 328 and electrically conductive tracks 322, 330.

In some examples, each discrete ceramic member 328 may form a discontinuous ceramic "island" layer between the first and second polymer layer 332, 334 so as to form a rivet to safeguard the integrity of the adhesion of the first and second polymer layer 332, 334 to each other or otherwise improve the overall adhesion of first and second polymer layers 332, 334 to each other.

In some examples, at least one of first polymer layer 332 and second polymer layer 334 may be biocompatible polymer layer and/or medical grade polymer layer. In one example, both polymer layers 332, 334 are made from Parylene-C.

The ceramic material of discrete ceramic members 328 and of ceramic layers 326, 321 may comprise at least one of SiN, SiOx, Si-Carbid, alumina or oxynitride. Discrete ceramic members 328 and ceramic layers 326, 321 may have substantially the same composition or different composition.

As shown in FIGS. 4 and 5, ceramic element 328 and metal tracks 322 and 330 do not contact each other in the example shown. Also, first and second polymer layer 332, 334 may surround ceramic element 328.

In some examples of the present disclosure, distal structure of a lead 300 may include "polymer only" areas, e.g., "Parylene only" areas. Such a distal structure may include of several areas where a continuous ceramic layer is not preferred. Instead, to provide some flexibility, "polymer only" areas are preferred due to mechanical reasons.

By ways of discrete ceramic members 328, the adhesion of polymer layers 332, 334 to each other is safeguarded, e.g., since the ceramic elements 328 form small "islands" of ceramic with superior adhesion properties. The ceramic "islands" or discrete ceramic members 328 may serve, in effect, as rivets to safeguard integrity of the polymer to polymer adhesion, here in the described example Parylene to Parylene adhesion.

In some examples, discrete ceramic members 328 are not continuous and as such there will not be a significant influence on the mechanical properties of the "polymer only" area. Also, cracks that might be induced in the ceramic because of mechanical handling of the thin film 301 may not propagate into the overall structure, but stop at the ceramic "island" boundary.

Thus, in some examples, by the use of discrete ceramic members 328 between the two polymer layers 332, 334 (e.g., two Parylene layers 332, 334), the integrity of the thin film 301 may be improved. The ceramic is not continuous though. Example reasons to implement a discontinuous ceramic layer between two polymer layers (e.g., two Parylene layers) include that discrete ceramic members 328 or ceramic "islands" may serve as a rivet to safeguard integrity of the polymer to polymer adhesion (e.g., Parylene to Parylene adhesion) or otherwise increase the adhesion between first polymer layer 332 and second polymer layer 334. Further, discrete ceramic members 328 or ceramic "islands" may serve to safeguard the integrity of thin film 301, e.g., as the discontinuous ceramic "islands" may prevent crack propagation on the ceramic. Also, the ceramic "islands" may prevent dissolution of the ceramic layer in the case that the edge of the ceramic "island" is exposed to the surface.

In some examples, the disclosure relates to a medical device system configured to at least one of deliver electrical stimulation to a patient or sense electrical activity of the patient, the system comprising a thin film. The thin film includes at least one electrode, at least one electrical contact, at least one electrically conductive track extending between the at least one electrode and the at least one electrical contact, a first polymer layer; a second polymer layer; and at least one discrete ceramic member located between the first and second polymer layers at a portion of the thin film between the at least one electrode and the at least one electrical contact, wherein the at least one discrete ceramic member does not surround the at least one conductive track at a portion of the thin film between the at least one electrode and the at least one electrical contact, and wherein the at least one discrete ceramic member is configured to increase adhesion between the first polymer layer and second polymer layer.

In another example, the disclosure relates to a method for forming an implantable medical lead configured to at least one of deliver electrical stimulation to a patient or sense electrical activity of the patient, the method comprising forming a first polymer layer; and forming a second polymer layer to form a thin film. The thin film comprises at least one electrode, at least one electrical contact, at least one electrically conductive track extending between the at least one electrode and the at least one electrical contact, the first polymer layer; the second polymer layer; and at least one discrete ceramic member located between the first and second polymer layers at a portion of the thin film between the at least one electrode and the at least one electrical contact, wherein the at least one discrete ceramic member does not surround the at least one conductive track at the portion of the thin film between the at least one electrode and the at least one electrical contact, and wherein the at least one discrete ceramic member is configured to increase adhesion between the first polymer layer and second polymer layer.

While the techniques described herein are suitable for systems and methods involving DBS therapies, and may be used treat such disorders as Parkinson's disease, Alzheimer's disease, tremor, dystonia, depression, epilepsy, OCD, and other disorders, the techniques are not so limited. One or more such techniques and systems may be applied to treat disorders such as chronic pain disorders, urinary or fecal incontinence, sexual dysfunction, obesity, mood disorders, gastroparesis or diabetes, and may involve other types of stimulation such as spinal cord stimulation, cardiac stimulation, pelvic floor stimulation, sacral nerve stimulation, peripheral nerve stimulation, peripheral nerve field stimulation, gastric stimulation, or any other electrical stimulation therapy. In some cases, the electrical stimulation may be used for muscle stimulation.

In addition, it should be noted that examples of the systems and techniques described herein may not be limited to treatment or monitoring of a human patient. In alternative examples, example systems and techniques may be implemented in non-human patients, e.g., primates, canines, equines, pigs, and felines. These other animals may undergo clinical or research therapies that my benefit from the subject matter of this disclosure.

The techniques of this disclosure may be implemented in a wide variety of computing devices, medical devices, or any combination thereof. Any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A server, client computing device, or any other computing device may also contain a more portable removable memory type to enable easy data transfer or offline data analysis. The techniques described in this disclosure, including those attributed to various modules and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, remote servers, remote client devices, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a computer-readable storage medium encoded with instructions. Instructions embedded or encoded in an article of manufacture including a computer-readable storage medium, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. The computer-readable storage medium may also be referred to as storage devices.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described herein. Any combination of the described operations or functions is contemplated. These and other examples are within the scope of the following claims.

The invention claimed is:

1. A medical device system configured to at least one of deliver electrical stimulation to a patient or sense electrical activity of the patient, the system comprising:
   a thin film including:
      at least one electrode,
      at least one electrical contact,
      at least one electrically conductive track extending between the at least one electrode and the at least one electrical contact,
      a first polymer layer;
      a second polymer layer, wherein, at a portion of the thin film between the at least one electrode and the at least one electrical contact, the first polymer layer and second polymer layer surround the at least one electrically conductive track; and
      at least one discrete ceramic member located between the first and second polymer layers at the portion of the thin film between the at least one electrode and the at least one electrical contact, wherein the at least one discrete ceramic member does not surround the at least one conductive track at the portion of the thin film between the at least one electrode and the at least one electrical contact, wherein the first polymer layer and second polymer layer surround the at least one discrete ceramic member at the portion of the thin film between the at least one electrode and the at least one electrical contact, wherein the at least one discrete ceramic member is in direct contact with the first polymer layer and the second polymer layer, and wherein the at least one discrete ceramic member is configured to increase adhesion between the first polymer layer and second polymer layer.

2. The system of claim 1, wherein the first polymer layer and the second polymer layer each comprise a medical grade polymer.

3. The system of claim 2, wherein the medical grade polymer comprises medical grade poly(p-xylylene) polymer.

4. The system of claim 1, wherein the at least one discrete ceramic member comprises at least one of SiN, SiOx, Si-Carbide, alumina, or oxynitride.

5. The system of claim 1, wherein each discrete ceramic member of the at least one discrete ceramic member is not in contact with the at least one electrode and the at least one electrical contact.

6. The system of claim 1, further comprising a ceramic layer between the at least one electrically conductive track and the first polymer layer, and between the electrically conductive track and the second polymer layer, wherein the ceramic layer surrounds the at least one electrically conductive track at the portion of the thin film between the at least one electrode and the at least one electrical contact.

7. The system of claim 6, wherein the ceramic layer comprises at least one of SiN, SiOx, Si-Carbide, alumina, or oxynitride.

8. The system of claim 6, wherein the ceramic layer and the at least one discrete ceramic member are formed of substantially a same ceramic composition.

9. The system of claim 1, wherein the at least one discrete ceramic member and the at least one electrically conductive track do not directly contact each other.

10. The system of claim 1, wherein a portion of the first polymer layer and second polymer layer are in direct contact with each other at the portion of the thin film between the at least one electrode and the at least one electrical contact.

11. The system of claim 1, further comprising a carrier core, wherein the thin film is wrapped around the carrier core to secure the thin film to the carrier core.

12. The system of claim 1, further comprising an implantable medical device, wherein the implantable medical device is configured to at least one of deliver electrical stimulation to a patient or sense electrical activity of the patient via the thin film.

13. The system of claim 1, wherein the at least one electrically conductive track extends between the at least one electrode and at least one electrical contact along a plane, and wherein the at least one discrete ceramic member is adjacent to the at least one conductive track along the plane.

14. A medical device system comprising:
an implantable medical device; and
an implantable medical lead, wherein the implantable medical device is configured to at least one of deliver electrical stimulation to a patient or sense electrical activity of the patient via the implantable medical lead, wherein the implantable lead comprises a thin film including:
at least one electrode,
at least one electrical contact,
at least one electrically conductive track extending between the at least one electrode and the at least one electrical contact,
a first polymer layer;
a second polymer layer, wherein, at a portion of the thin film between the at least one electrode and the at least one electrical contact, the first polymer layer and second polymer layer surround the at least one electrically conductive track; and
at least one discrete ceramic member located between the first and second polymer layers at the portion of the thin film between the at least one electrode and the at least one electrical contact, wherein the at least one discrete ceramic member does not surround the at least one conductive track at the portion of the thin film between the at least one electrode and the at least one electrical contact, wherein the first polymer layer and second polymer layer surround the at least one discrete ceramic member at the portion of the thin film between the at least one electrode and the at least one electrical contact, wherein the at least one discrete ceramic member is in direct contact with the first polymer layer and the second polymer layer, and wherein the at least one discrete ceramic member is configured to increase adhesion between the first polymer layer and second polymer layer.

15. A method for forming an implantable medical lead configured to at least one of deliver electrical stimulation to a patient or sense electrical activity of the patient, the method comprising:
forming a first polymer layer; and
forming a second polymer layer to form a thin film, wherein the thin film comprises:
at least one electrode,
at least one electrical contact,
at least one electrically conductive track extending between the at least one electrode and the at least one electrical contact,
the first polymer layer,
the second polymer layer, wherein, at a portion of the thin film between the at least one electrode and the at least one electrical contact, the first polymer layer and second polymer layer surround the at least one electrically conductive track, and
at least one discrete ceramic member located between the first and second polymer layers at the portion of the thin film between the at least one electrode and the at least one electrical contact, wherein the at least one discrete ceramic member does not surround the at least one conductive track at the portion of the thin film between the at least one electrode and the at least one electrical contact, wherein the first polymer layer and second polymer layer surround the at least one discrete ceramic member at the portion of the thin film between the at least one electrode and the at least one electrical contact, wherein the at least one discrete ceramic member is in direct contact with the first polymer layer and the second polymer layer, and wherein the at least one discrete ceramic member is configured to increase adhesion between the first polymer layer and second polymer layer.

16. The method of claim 15, wherein the first polymer layer and the second polymer layer each comprise a medical grade polymer.

17. The method of claim 16, wherein the medical grade polymer comprises medical grade poly(p-xylylene) polymer.

18. The method of claim 15, wherein the at least one discrete ceramic member comprises at least one of SiN, SiOx, Si-Carbide, alumina, or oxynitride.

19. The method of claim 15, wherein each discrete ceramic member of the at least one discrete ceramic member is not in contact with the at least one electrode and the at least one electrical contact.

20. The method of claim 15, further comprising forming a ceramic layer between the at least one electrically conductive track and the first polymer layer, and between the at least one electrically conductive track and the second polymer layer, wherein the ceramic layer surrounds the at least one electrically conductive track at the portion of the thin film between the at least one electrode and the at least one electrical contact.

21. The method of claim 20, wherein the ceramic layer and the at least one discrete ceramic member are formed of substantially a same ceramic composition.

22. The method of claim 15, wherein a portion of the first polymer layer and second polymer layer are in direct contact with each other at the portion of the thin film between the at least one electrode and the at least one electrical contact.

* * * * *